United States Patent [19]

Baudys et al.

[11] Patent Number: 5,726,154

[45] Date of Patent: Mar. 10, 1998

[54] STABILIZATION AND ORAL DELIVERY OF CALCITONIN

[75] Inventors: Miroslav Baudys; Sung Wan Kim, both of Salt Lake City, Utah

[73] Assignee: University of Utah Research Foundation, Salt Lake City, Utah

[21] Appl. No.: 671,870

[22] Filed: Jun. 28, 1996

[51] Int. Cl.$^6$ .......................... A61K 38/00; A61K 38/02; A61K 38/30; C07K 5/00

[52] U.S. Cl. ........................... 514/12; 514/2; 530/307

[58] Field of Search .......................... 514/2, 12; 530/307

[56] References Cited

U.S. PATENT DOCUMENTS

| | | | |
|---|---|---|---|
| 4,654,132 | 3/1987 | Takagi et al. | 204/182.8 |
| 4,954,342 | 9/1990 | Lattanzi et al. | 424/436 |
| 5,002,771 | 3/1991 | Purkaystha et al. | 424/433 |
| 5,120,710 | 6/1992 | Liedtke | 514/3 |
| 5,145,684 | 9/1992 | Liversidge et al. | 424/489 |
| 5,183,746 | 2/1993 | Shaked et al. | 435/69.51 |
| 5,288,497 | 2/1994 | Stanley et al. | 424/440 |
| 5,288,498 | 2/1994 | Stanley et al. | 424/440 |
| 5,350,741 | 9/1994 | Takada | 514/3 |
| 5,430,021 | 7/1995 | Rudnic et al. | 514/14 |
| 5,444,041 | 8/1995 | Owen et al. | 514/2 |
| 5,571,788 | 11/1996 | Arvinte et al. | 514/12 |
| 5,633,226 | 5/1997 | Owen et al. | 514/2 |

FOREIGN PATENT DOCUMENTS 0 490 549 A1  6/1992  European Pat. Off. .

OTHER PUBLICATIONS

J. DeRose, M.D., *Response of Paget's Disease to Porcine and Salmon Calcitonins*, 56 Amer. Journal of Medicine, 858–866 (1974).

V. Fatourechi, M.D. et al. *Salmon Calcitonin in the Treatment of Postmenopausal Osteoporosis*, 107 Annals of Internal Medicine 923–925 (1987).

(List continued on next page.)

*Primary Examiner*—Cecilia J. Tsang
*Assistant Examiner*—Michael L. Borin
*Attorney, Agent, or Firm*—Thorpe, North & Western, L.L.P.

[57] ABSTRACT

Compositions and methods for stabilization and oral delivery of human calcitonin are described. An aqueous liquid composition for stable storage of human calcitonin comprises an aqueous mixture of SDS and an organic acid. An nonaqueous liquid composition for stable storage of human calcitonin comprises about 90–100% by volume of a mixture of $C_8/C_{10}$ mono- and di-glycerides and about 0–10% by volume of a polar, nonaqueous solvent. Both of these stabilized human calcitonin formulations provided significant intestinal absorption of calcitonin.

25 Claims, 10 Drawing Sheets

OTHER PUBLICATIONS

D.J. Hosking, *Treatment of Sever Hypercalcaemia with Calcitonin*, 2, Metab. Bone Dis. & Rel. Res. 207–212 (1980).

H. E. Gruber et al., *Long–Term Calcitonin Therapy in Postmenopausal Osteoporosis*, 33 Metabolism 295–303 (1984).

J. H. Carstens, Jr. et al., *Future Horizons for Calcitonin: A U.S. Perspective*, 49 Calcif Tissue Int. S2–S6 (1991).

S. J. Heiber, et al., *In–Vivo Buccal Delivery of Calcitonin*, 28 J. Control. Release 269–271 (1994).

J. Hastewell et al., *Absorption of human calcitonin across the rat colon in vivo*, 82, Clinical Science 589–594 (1992).

K. Overgaard et al., *Rectal Salmon Calcitonin for the Treatment of Postmenopausal Osteoporosis*, 51, Calcif. Tissue Int. 184–188 (1992).

S. Kobayashi et al., *Pulmonary Delivery of Salmon Calcitonin Dry Powders Containing Absorption Enhancers in Rats*, 13 Pharmaceutical Research 80–83 (1996).

J. P. Devogelaer et al., *Comparison of the Acute Biological Action of Injectable Salmon Calcitonin and an Injectable and Oral Calcitonin Analogue* (1994).

R. Muff, Ph.D., et al., *Efficacy of Intranasal Human Calcitonin in Patients with Paget's Disease Refractory to Salmon Calcitonin* 89 The American Journal of Medicine 181–184 (1990).

P. Sieber et al., *255 Menschliches Calcitonin. VI). Die Synthese von Calcitonin $M^2$)*, 53 Helvetica Chemica Acta 2135–2150 (1970).

T. Arvinte et al., *The Structure and mechanism of Fomration of Human Calcitonin Fibrils*, 268 The Journal of Biological Chemistry 6415–6422 (1993).

R. Maier, et al., *Analogues of Human Calcitonin*, 85 Acta Endocrinlogica 102–108 (1977).

Paul Becher and Martin J. Schick, *Macroemulsions* Nonionic Surfactant Physical Chemistry 439–56 (Marcel Dekker, NW 1987).

A. Helenius & K. Simons, *Solubilization of Membranes by detergents*, 415 Biochim. Biophys, Acta 29–79 (1975).

L. Hovgaard et al., *Insulin Stabilization and GI Absorption* 19 J. Control. Release 99–108 (1992).

M. Baudys et al., *Stabilization and Intestinal Absorption of Human Calcitonin*, 1266 Journal of Controlled Release 1–7 (1996).

Karyn F. Thompson and Lila M. Gierasch. *Conformation of a Peptide Solubilizate in a Reversed Micelle Water Pool*, 106 J. Am. Chem. Soc. 3648–3652 (1984).

P. L. Luisi et al, *Reverse micelles as hosts for proteins and small molecules*, 947 Biochimica et Biophysica Acta 109–246 (1988).

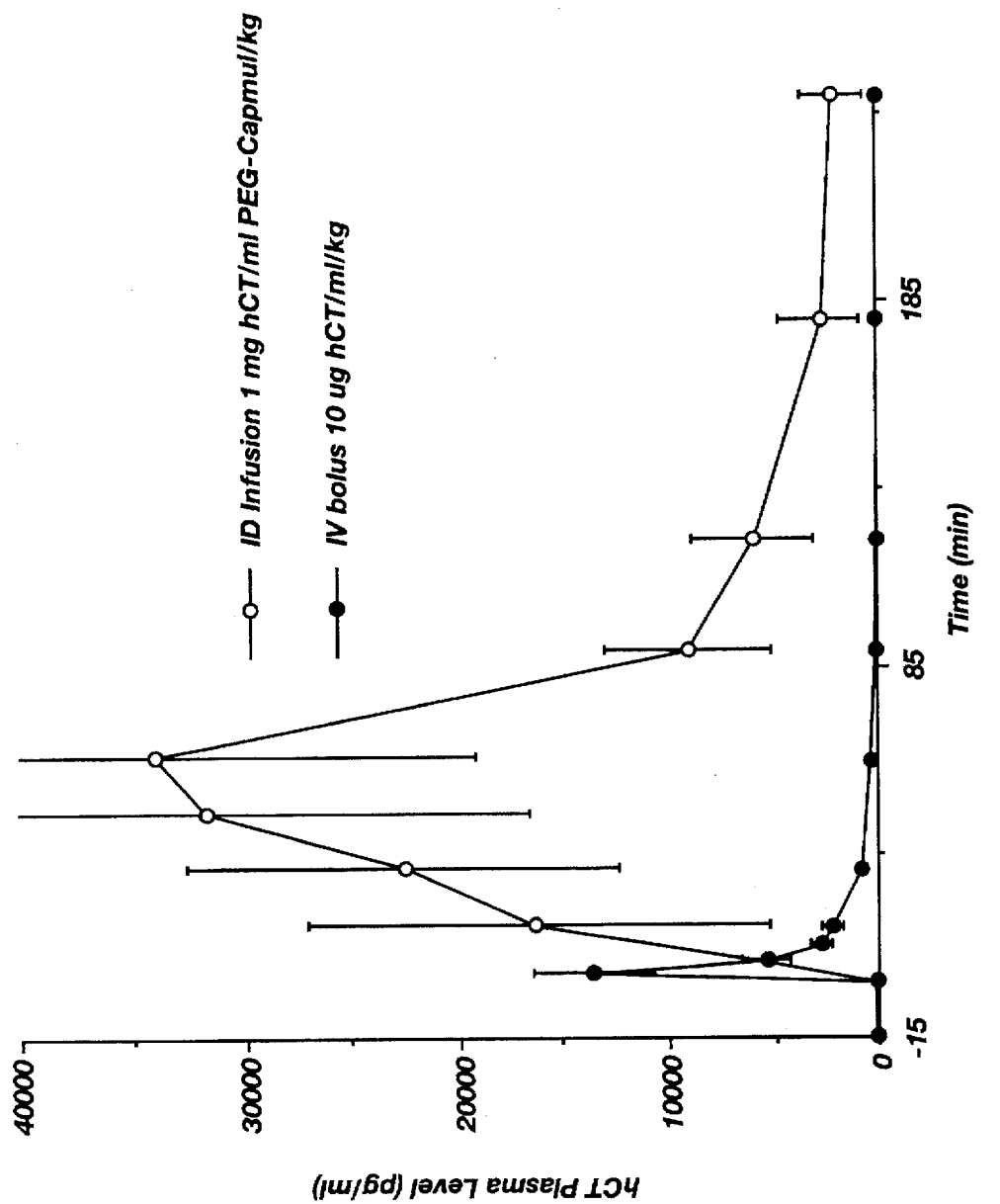

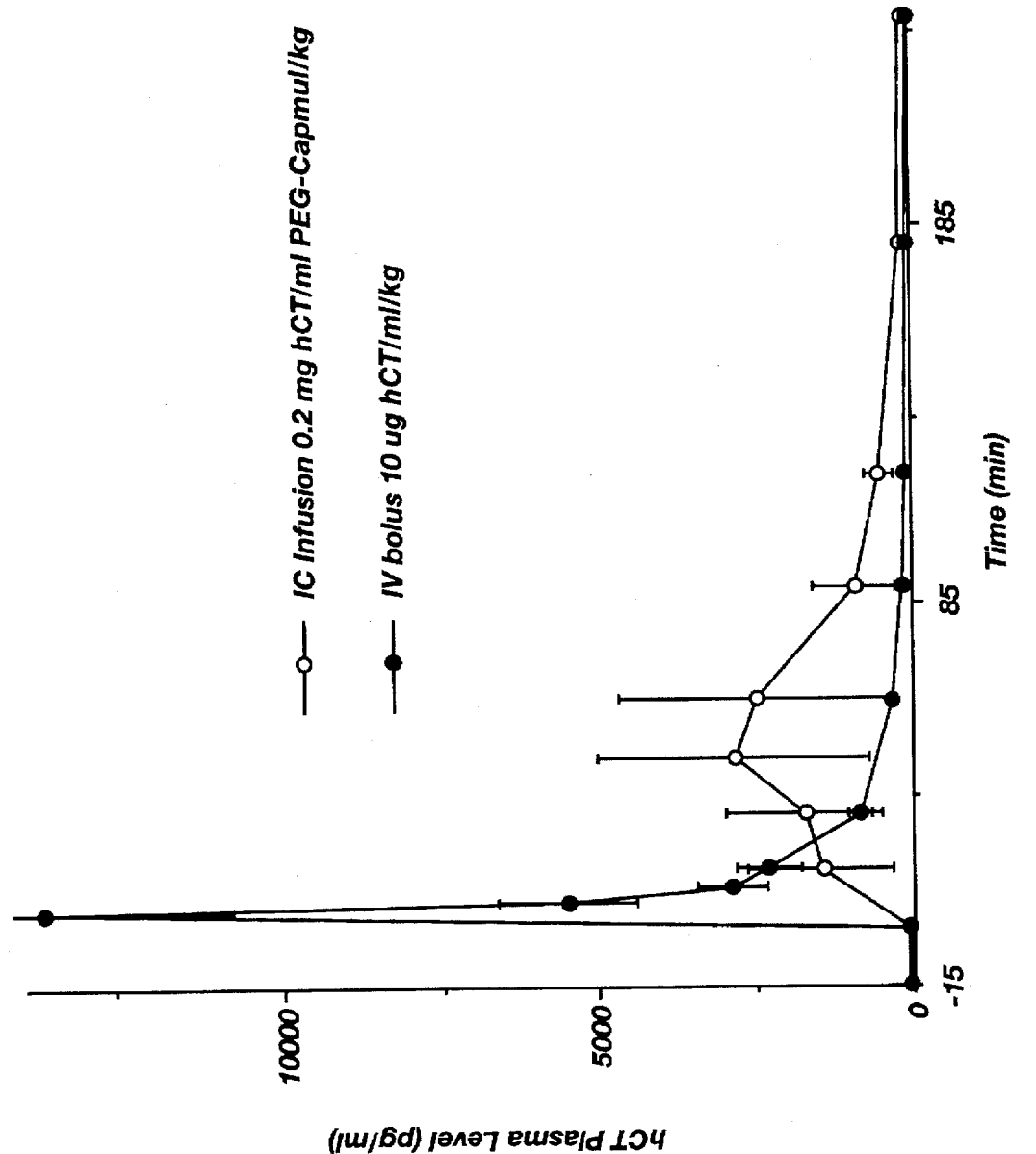

STABILIZATION AND ORAL DELIVERY OF CALCITONIN

BACKGROUND OF THE INVENTION

This invention relates to oral delivery of calcitonin. More particularly, the invention relates to compositions and methods for stabilizing human calcitonin in solution and for delivering human calcitonin orally.

Many biologically active peptides and proteins have recently become available for therapeutic use because of enormous progress in biotechnology. Despite the availability of these therapeutic peptides and proteins, many problems associated with the application of these drugs remain unsolved. These problems generally relate to (1) the long-term physical and chemical instability of therapeutically active peptides and proteins, especially in solution, and (2) appropriate and effective administration to the body, with consideration given to endogenous regulation of the peptides and proteins.

Currently, bioactive peptides and proteins are commonly administered parenterally, usually with a number of side effects. Large and frequent doses are often required to maintain therapeutically sufficient levels of such drugs. This makes parenteral administration undesirable for the chronic treatment necessary in many conditions and disease states. Many alternative routes of administration, such as rectal, nasal, and buccal, are being investigated, but the oral route remains the clinically most acceptable.

Orally administered peptides are subject to degradation by digestive proteolytic enzymes, namely pepsin in the stomach and trypsin, chymotrypsin, elastase, and others in the small intestine. Such degradation hinders oral bioavailability of peptide drugs. Nevertheless, the major obstacle to oral delivery of peptide drugs is absorption through the intestinal wall because of low permeability. To improve intestinal absorption of poorly or irregularly absorbed drugs including peptides, absorption enhancers, which perturb the barrier properties of mucosal membranes, may be employed.

Human calcitonin (hCT) is a peptide hormone containing 32 amino acid residues. Calcitonin lowers blood calcium levels by increasing urinary calcium excretion and inhibiting bone resorption. M. Azria, The Calcitonins (1989). It is used therapeutically to treat Paget's disease, osteoporosis, and hypercalcemias of different origins. J. deRose et al., Response of Paget's disease to porcine and salmon calcitonins: effects of long-term treatment, 56 Am. J. Med. 858–66 (1974); V. Fatourechi & H. Hunter, Salmon calcitonin in the treatment of postmenopausal osteoporosis, 107 Ann. Intern. Med. 923–25 (1987); D. J. Hosking, Treatment of severe hypercalcemia with calcitonin, 2 Metab. Bone Dis. Relat. Res. 207–12 (1980). As with other peptide drugs, calcitonin is usually administered parenterally, however this results in a number of gastric and vascular side effects. H. W. Gruber et al., Long-term calcitonin therapy in postmenopausal osteoporosis, 33 Metabolism 295–303 (1984). The nasal route of administration is better tolerated, but local nasal irritation is common. S. J. Carstens, Jr. & J. D. Feinblatt, Future horizons for calcitonin: A U.S. perspective, 49 Calcif. Tissue Int. S2–S6 (Supp. 2, 1991). To improve therapy, many studies have focused on alternative routes of administration, such as buccal, colonic, rectal, and pulmonary routes. S. J. Heiber et al., In-vivo buccal delivery of calcitonin, 28 J. Control. Release 269–71 (1994); J. Hastewell, et al., Absorption of human calcitonin across the rat colon, 82 Clin. Sci. 589–94 (1992); K. Overgaard et al., Rectal salmon calcitonin for the treatment of postmenopausal osteoporosis, 51 Calcif. Tissue Int. 184–88 (1992); S. Kobayashi et al., Pulmonary delivery of salmon calcitonin dry powders containing absorption enhancers in rats, 13 Pharm. Res. 80–83 (1996). Very recently, an oral dosage form of a chemically modified calcitonin (ASC 710) was shown to be clinically effective and comparable to salmon calcitonin (sCT) injection. Very high doses (20 mg/single dose) were necessary, however, to obtain clinical relevance. J. P. Devogelaer et al., Comparison of the acute biological action of injectable salmon calcitonin and an injectable and oral calcitonin analogue, 55 Calcif. Tissue Int. 71–73 (1994).

Both hCT and sCT are clinically available, but hCT must be administered at doses ranging from 0.25 to 1.0 mg/day due to its lower potency compared to sCT. Human calcitonin, however, does not elicit a neutralizing antibody response after prolonged administration, as does sCT. R. Muff et al., Efficacy of indranasal human calcitonin in patients with Paget's disease refractory to salmon calcitonin, 89 Am. J. Med. 181–84 (1990). On the other hand, the therapeutic use of hCT is hampered by its physical instability in aqueous solutions, especially near neutral pH. In solution, hCT has a tendency to aggregate and precipitate. The resulting turbid, viscous solution consists of associated 80 Å-diameter fibrils. P. Seiber et al., Human calcitonin: synthesis of calcitonin, 53 M. Helv. Chim. Acta 2135–50 (1970). More detailed physico-chemical investigation reveals that the fibrillation process can be explained by a double nucleation mechanism. T. Arvinte et al., The structure and mechanism of formation of human calcitonin fibrils, 268 J. Biol. Chem. 6415–22 (1993). Electrostatic interactions between calcitonin monomers are likely to play an important role in the initial nucleation step. In this context, the different pI values of hCT (8.7) and sCT (10.4) seem to be responsible for the strong fibrillation properties of hCT and high solution stability of sCT around neutral pH. R. Maier et al., Analogues of human calcitonin, 85 Acta Endocrinol. 102–108 (1977). It has been reported that hCT solutions comprising a dilute acid are stable for several months, T. Arvinte et al., EP 490549, but this has been shown to be unreliable.

In view of the foregoing, it will be appreciated that development of compositions and methods for stabilizing human calcitonin during storage in solutions and for oral delivery of human calcitonin would be a significant advancement in the art.

BRIEF SUMMARY OF THE INVENTION

It is an object of the present invention to provide compositions and methods for stabilizing human calcitonin during storage in solutions.

It is also an object of the invention to provide compositions and methods for oral delivery of human calcitonin.

It is another object of the invention to provide compositions and methods for effective intestinal absorption of human calcitonin after oral delivery.

These and other objects can be accomplished by providing a human-calcitonin-containing liquid composition for stable storage of human calcitonin for at least about 6 months at about 4°–25° C. and for intestinal delivery of human calcitonin comprising a selected concentration of human calcitonin dissolved in a liquid medium selected from the group consisting of (a) an aqueous mixture of an effective amount of SDS and an effective amount of an organic acid; and (b) about 90–100% by volume of a mixture of $C_8/C_{10}$ mono- and di-glycerides and about 0–10% by volume of a polar, nonaqueous solvent.

When the liquid medium is an aqueous mixture of an effective amount of SDS and an effective amount of an organic acid, the selected concentration of human calcitonin is preferably up to about 10 mg/ml and more preferably about 0.5–2.0 mg/ml. The effective amount of SDS is preferably about 0.24% to 10% by weight and more preferably about 0.24% to 1% by weight. The effective amount of organic acid is preferably about 0.005% to 1% by weight and more preferably about 0.01% to 1% by weight.

When the liquid medium is about 90–100% by volume of a mixture of $C_8/C_{10}$ mono- and di-glycerides and about 0–10% by volume of a polar, nonaqueous solvent, preferred embodiments include (a) a mixture of $C_8/C_{10}$ mono- and di-glycerides and (b) about 90–99% by volume of a mixture of $C_8/C_{10}$ mono- and di-glycerides and about 1–10% by volume of a polar, nonaqueous solvent. Preferably, the polar, nonaqueous solvent is a member selected from the group consisting of ethylene glycol, propylene glycol (PPG), polyethylene glycol 200 (PEG 200), dimethylformamide, and dimethylsulfoxide.

A method for delivering human calcitonin for intestinal absorption into the body comprises the steps of:

(a) providing a human-calcitonin-containing liquid composition comprising a selected concentration of human calcitonin dissolved in a liquid medium selected from the group consisting of (i) an aqueous mixture of an effective amount of SDS and an effective amount of an organic acid; and (ii) about 90–100% by volume of a mixture of $C_8/C_{10}$ mono- and di-glycerides and about 0–10% by volume of a polar, nonaqueous solvent; and (b) administering the human-calcitonin-containing liquid composition such that the human-calcitonin-containing liquid contacts the intestinal mucosa and the human calcitonin is absorbed therethrough.

Preferably, the administering step comprises orally administering the human-calcitonin-containing composition.

BRIEF DESCRIPTION OF THE SEVERAL VIEWS OF THE DRAWINGS

FIGS. 4A–B show plasma hCT levels (FIG. 4A) and corresponding plasma calcium levels (FIG. 4B) after bolus IV or 1 hour IC infusion administration of hCT formulations: ○—IC infusion of 1.0 mg hCT/ml 90% (v/v) CAPMUL MCM, 10% (v/v) PEG 200/kg; ●—IV bolus of 10 µg hCT/ml/kg.

FIGS. 5A–B show plasma hCT levels (FIG. 5A) and corresponding plasma calcium levels (FIG. 5B) after bolus IV or 1 hour IC infusion administration of hCT formulations: ○—IC infusion of 0.2 mg hCT/ml 90% (v/v) CAPMUL MCM, 10% (v/v) PEG 200/kg; ●—IV bolus of 10 µg hCT/ml/kg.

DETAILED DESCRIPTION

Figure 1A:
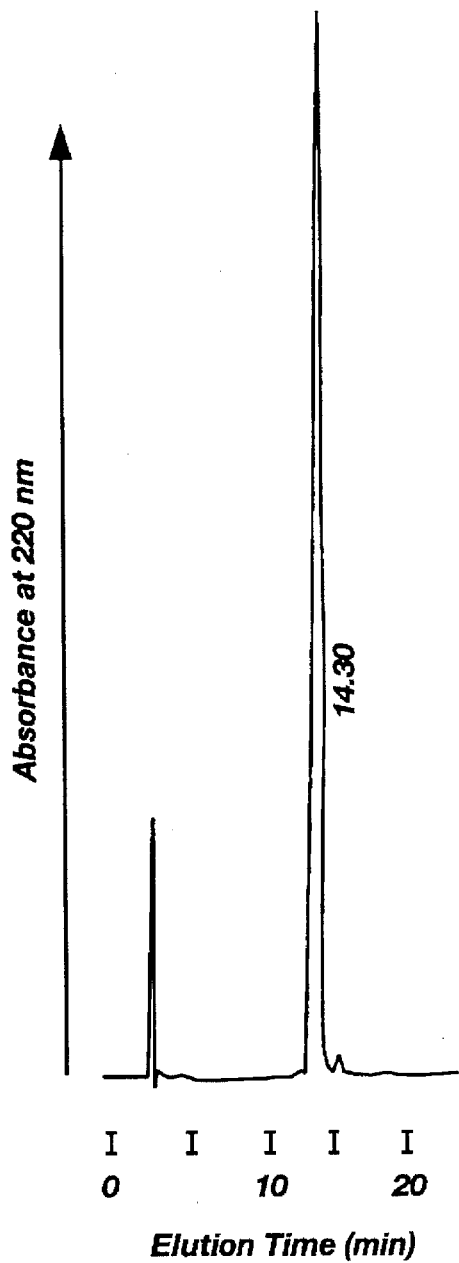
FIGS. 1A–B show, respectively, HPLC analysis of hCT in 0.01% acetic acid and in 0.01% acetic acid containing 1.0% SDS.

Before the present compositions and methods for orally delivering and stabilizing human calcitonin in solutions are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise.

In describing and claiming the present invention, the following terminology will be used in accordance with the definitions set out below.

As used herein, "peptide" means peptides of any length and includes proteins. The terms "polypeptide" and "oligopeptide" are used herein without any particular intended size limitation, unless a particular size is otherwise stated.

As used herein, "stable," "stabilizing," and similar terms refer to inhibiting the precipitation, fibrillation, or gelation of human calcitonin molecules upon storage in a liquid medium at a temperature of about 4°–25° C. Human calcitonin is considered "stable" or "stabilized" in a selected liquid medium when no precipitation, fibrillation, or gellation is detected upon storage at a temperature of about 4°–25° C. for a period of at least about 6 months.

As used herein, "ambient temperature" or "room temperature" refers to a nominal temperature of about 25° C.

As used herein, "effective amount" means an amount of SDS or organic acid sufficient to provide a selected effect and performance for stabilizing a selected amount of human calcitonin. For example, as will be shown below, 1 mg/ml of human calcitonin is stabilized for greater than 1 year at ambient temperature in a solution containing 0.01% acetic acid and ≧0.4% (w/v) SDS, whereas 2 mg/ml human calcitonin is stabilized for greater than 1 year at ambient temperature in a solution containing 0.01% and ≧0.6% (w/v) SDS. Higher concentrations of human calcitonin can be stabilized with corresponding higher concentrations of SDS, limited only by the solubility thereof.

As used herein, "HLB" or "hydrophilic-lipophilic balance" means an empirical quantity, on an arbitrary scale, that is a measure of the polarity of a surfactant or mixture of surfactants. See P. Becher et al., Nonionic Surfactant Physical Chemistry 439–56 (Marcel Dekker, N.Y. 1987), hereby incorporated by reference. It is a widely known and widely used term in the art.

As used herein, "organic acid" refers to pharmaceutically acceptable, carbon-containing acids, such as carboxylic acids. For example, preferred organic acids according to the present invention include monocarboxylic, dicarboxylic, tetracarboxylic, and hydroxycarboxylic acids and phenols. More preferred organic acids include formic acid, acetic acid, ascorbic acid, malonic acid, glutaric acid, adipic acid, citric acid, L-α-tartaric acid, DL-tartaric acid, ethylenediamine tetraacetic acid, and phenol. Acetic acid is most preferred.

As used herein, "polar, nonaqueous solvent" and similar terms refer to polar, non-toxic, nonaqueous solvents that are miscible in medium chain ($C_8/C_{10}$) mono- and di-glycerides, such as ethylene glycol, propylene glycol, polyethylene glycol 200 (average molecular weight=200,000), dimethylformamide, and dimethylsulfoxide. Preferred polar, nonaqueous solvents include ethylene glycol, propylene glycol, and polyethylene glycol 200.

Stability of Human Calcitonin

To develop an effective oral liquid dosage form for human calcitonin, the stability of hCT solutions over long periods of time must be greatly improved. Since hCT is highly unstable in aqueous solutions of neutral or basic pH, acidic formulations were investigated to determine whether increased stability could be obtained. Lyophilized hCT (Suntory Ltd., Japan) was stored at −20° C. until use, whereupon the dry calcitonin was carefully dissolved in a selected solution according to the present invention by gentle hand shaking or stirring with a magnetic stir bar. Salts or buffers should not be present in the storage solutions.

Samples (1–2 ml) containing 0.2–10 mg/ml of hCT in aqueous formulations were prepared and then maintained in 4 ml borosilicate vials at ambient temperature or at 4° C. The samples were checked periodically for the presence of a precipitate, a gel, or turbidity, which are indicative of fibrillation. In cases of formulations in which the hCT was very unstable, changes in turbidity could be followed over time by spectrophotometry at 340 nm. T. Arvinte et al., The structure and mechanism of formation of human calcitonin fibrils, 268 J. Biol. Chem. 6415–22 (1993), hereby incorporated by reference. In some cases, the concentration of unaggregated hCT was determined using reversed-phase HPLC (Waters modular system with Waters model 745 integrator, Bedford, Mass.) on a Vydac $C_4$ column (4.6 mm×25 cm) equilibrated at a flow rate of 1 ml/min with 0.1% (v/v) trifluoroacetic acid containing 30% (v/v) acetonitrile. Five minutes after injection of a 100 µl sample, a linear gradient of 0.67% acetonitrile/min was applied. Absorbance (at 220 nm) of the eluent was recorded and processed to quantify the amount of hCT injected.

Table 1 shows the effect of dilute acetic acid on stability of 2 mg/ml hCT upon storage in a liquid formulation.

TABLE 1

| | Stabilization period | |
|---|---|---|
| Storage medium | Ambient Temp. | 4° C. |
| PBS, pH 7.0 | 2 h | — |
| 0.01% (w/v) acetic acid | 4 days | 14 days |
| 0.1% (w/v) acetic acid | 10 days | 30–40 days |
| 1.0% (w/v) acetic acid | 1–2 months | — |

Thus, at ambient temperature, increased stabilization of hCT in solution was observed with increasing acetic acid concentration. At 4° C., the increase in "stabilization period," i.e. the length of time that hCT remains in solution before fibrillation is detected, was even greater than at ambient temperature. The results reported by T. Arvinte et al., EP 490549, of stable formulations containing 5 mg/ml hCT in 0.0001%–1.0% acetic acid for 8 months could not be duplicated.

The stabilizing effect of acetic acid on hCT in aqueous solution was found to be concentration dependent. That is, as the hCT concentration increased, under otherwise identical conditions, the stabilization period decreased in accord with the observations of T. Arvinte et al., The structure and mechanism of formation of human calcitonin fibrils, 268 J. Biol. Chem. 6415–22 (1993).

The influence on hCT stability of different classes of surfactants and/or penetration enhancers under mildly acidic conditions was also determined. Bile salts (0.5–1.0%), including taurocholate, deoxycholate, and glycocholate, generally did not stabilized hCT in aqueous solution, since gel formation at either neutral or acidic pH occurred within 1 h. Table 2 summarizes the effects on hCT stability of 0.01% acetic acid together with various concentrations of an anionic detergent, sodium dodecyl sulfate (SDS).

TABLE 2

| Calcitonin conc. (mg/ml) | % (w/v) SDS | Stabilization period |
|---|---|---|
| 0.2 | 0.2 | 3 weeks |
|  | ≧0.3 | ≧1 year |
| 0.5 | 0.2 | 2 weeks |
|  | ≧0.3 | ≧1 year |
| 1.0 | 0.2 | 2 weeks |
|  | ≧0.4 | ≧1 year |
| 2.0 | 0.1 | 1–2 h |
|  | 0.4 | 2 weeks |
|  | 0.6 | ≧1.5 years |
|  | 1.0 | ≧2 years |
| 5.0 | 1.0 | 2 weeks |
| 10.0 | 1.0 | 2 days |

Thus, an effective amount of SDS in combination with acetic acid produced a prolonged stabilization effect on hCT in solution. This is an unexpected result in view of the strong protein denaturing and inactivating activity of SDS. E.g. Takagi et al., U.S. Pat. No. 4,654,132.

Figure 1B:
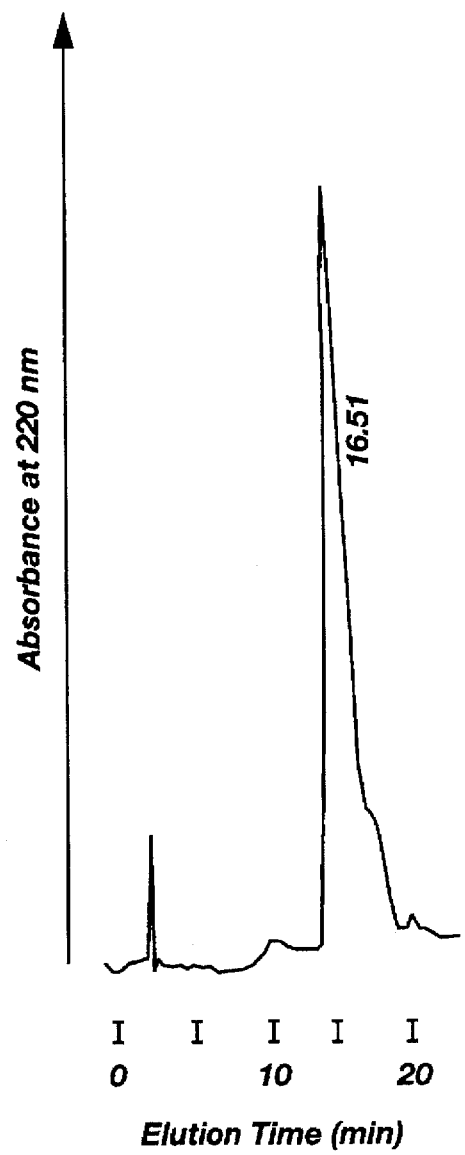

HPLC analysis of hCT in 0.01% acetic acid or in 0.01% acetic acid containing 1.0% SDS was performed to determine the state and concentration of unaggregated hCT in such formulations. FIGS. 1A and 1B show that a very stable complex was formed between the calcitonin and SDS since the calcitonin peak in the presence of SDS (FIG. 1B) eluted significantly later than in the absence of SDS (FIG. 1A) under identical chromatographic conditions. Moreover, the HPLC profiles and the UV spectra were not altered after 8 months of storage at ambient temperature.

The effect of the ratio of hCT concentration to SDS concentration was also investigated, as shown in Table 2. For example, when hCT concentration was increased and the SDS concentration was kept constant at 1%, the stabilization period dropped abruptly. On the other hand, when the hCT concentration was reduced to 0.2–1.0 mg/ml, an SDS concentration of 0.3% or greater provided prolonged (≧1 year) hCT stability in aqueous solution.

The critical micelle concentration (CMC) for SDS in water at room temperature is 0.24%. A. Helenius & K. Simons, Solubilization of membranes by detergents, 415 Biochim. Biophys. Acta 29–79 (1975). This suggests that the long-term stabilization effect of SDS on hCT may be dependent on the presence of SDS micelles. It is further suggested that when the number of hCT potential binding sites of SDS micelles is exhausted, as at high hCT concentrations, the fraction of hCT that does not form a complex with SDS in solution precipitates and forms fibrils.

Because of an anticipated need to enhance absorption of hCT through the intestinal mucosa upon oral administration, absorption enhancers other than SDS were also investigated for ability to stabilize hCT. It has been determined that certain nonaqueous solutions comprising low HLB surfactants and, optionally, a polar solvent, are effective in stabilizing hCT during storage. Lyophilized calcitonin was carefully dissolved in a mixture of medium chain ($C_8/C_{10}$) mono- and di-glycerides, such as CAPMUL MCM (Karlshamns Lipid Specialties, Columbus, Ohio), over a period of about 1 week by gentle, occasional hand shaking. Alternatively, the freeze dried human calcitonin was carefully dissolved in a selected polar solvent by gently hand shaking or stirring with a magnetic stir bar followed by mixing with a mixture of medium chain mono- and di-glycerides. Table 3 shows the results of several formulations comprising CAPMUL MCM or a mixture of CAPMUL MCM and a polar, CAPMUL MCM-miscible, nontoxic, nonaqueous solvent, such as ethylene glycol, propylene glycol, polyethylene glycol 200, dimethylformamide, or dimethylsulfoxide.

TABLE 3

| Formulation | Stabilization period |
| --- | --- |
| 1 mg hCT/ml CAPMUL MCM | >1 year |
| 1 mg hCT/ml 95% (v/v) CAPMUL MCM, 5% (v/v) ethylene glycol | >6 months |
| 0.5 mg hCT/ml 95% (v/v) CAPMUL MCM, 5% (v/v) ethylene glycol | >6 months |
| 1 mg hCT/ml 95% (v/v) CAPMUL MCM, 5% (v/v) propylene glycol | >1 year |
| 0.5 mg hCT/ml 95% (v/v) CAPMUL MCM, 5% (v/v) propylene glycol | >1 year |
| 1 mg hCT/ml 90% (v/v) CAPMUL MCM, 10% (v/v) propylene glycol | >6 months |
| 0.5 mg hCT/ml 90% (v/v) CAPMUL MCM, 10% (v/v) propylene glycol | >6 months |
| 1 mg hCT/ml 90% (v/v) CAPMUL MCM, 10% (v/v) PEG 200 | >6 months |
| 0.5 mg hCT/ml 90% (v/v) CAPMUL MCM, 10% (v/v) PEG 200 | >6 months |

These results show that hCT is soluble and stable in a composition comprising at least about 90% by volume of a mixture of $C_8/C_{10}$ mono- and di-glycerides and optionally up to about 10% by volume of a polar, nonaqueous solvent.

hCT Intestinal Absorption

Some of the liquid hCT formulations described above, especially formulations that exhibited activity for long-term stabilization of hCT, were investigated for hCT intestinal absorption.

In vivo absorption of hCT by the duodenum or colon was determined in male Sprague-Dawley rats weighing 300±50 g. One day prior to being used in an experiment, the rats were anesthetized with ether and a small tube was implanted into the duodenum or colon as described in L. Hovgaard et al., Insulin stabilization and GI absorption, 19 J. Control. Release 99–108 (1992), hereby incorporated by reference. The rats were then subjected to fasting overnight and allowed water ad libitum. On the next day, the rats were anesthetized with sodium pentobarbital (35 mg/kg, IP) and a jugular catheter was implanted. Two control blood samples were taken at −15 and −5 minutes. Various calcitonin solutions were then administered by the intraduodenal (ID) or intracolonic (IC) route, either as a bolus or a 1 h infusion using a precision syringe pump (Sage Instruments, Cambridge, Mass.). Blood samples (0.4 ml) were periodically withdrawn from jugular catheters into centrifuge tubes containing 5 μl (25 U) of heparin (Elkins-Sinn, Cherry Hill, N.J.). The samples were centrifuged (10,000 rpm, 4° C.) and the plasma stored at −20° C. until being assayed for hCT and calcium concentrations.

Plasma hCT levels were determined using a commercial RIA kit (Diagnostic Products Corporation, Los Angeles, Calif.). The samples were suitably diluted before analysis. All assays were run in duplicate with a standard curve for each assay. Plasma hCT levels were expressed in units of pg/ml.

Calcium plasma levels were measured spectrophotometrically at λ=575 nm using a commercial colorimetric kit (Sigma Chemical Co., St. Louis, Mo.) according to the manufacturer's instructions. All assays were also run in duplicate with a new standard curve for each assay. The plasma calcium concentration was expressed in units of mg/dl.

Six animals were used for each intestinal absorption experiment with results expressed as mean±SD. For the assessment of statistical significance of difference, Student's t-test and one- and two-way analysis of variance were used. Results were termed significant at P<0.02. Since all results of absorption experiments (hCT and calcium plasma levels and corresponding area under the curve (AUC) levels) were significantly different from controls (no hCT administered), no specific comments on statistical analysis are further provided. The area under the plasma hCT concentration versus time curves (AUC) from time zero to the last measurable point was calculated by the trapezoidal method as described in M. Rowland & T. N. Tozer, Clinical Pharmacokinetics: Concepts and Applications (1989), hereby incorporated by reference. Bioavailability, F, the fraction of dose absorbed, was calculated using the following equation:

$$\% F = \frac{AUC_{non-i.v.}}{AUC_{i.v.}} \times \frac{dose_{i.v.}}{dose_{non-i.v.}} \times 100$$

Table 4 shows the bioavailabilities of human calcitonin in formulations administered via the duodenum (by bolus) or the colon (1 h infusion).

TABLE 4

| Formulation | Dose (mg/kg) | Route | F (%) |
| --- | --- | --- | --- |
| 0.01% HOAc[a] | 2.0 | ID | 0.00 |
| 1% SDS in 0.01% HOAc | 2.0 | ID | 0.94 |
| 1% SDS in 0.01% HOAc | 2.0 | IC | 11.4 |
| 1% SDS, 0.01% HOAc | 0.2 | IC | 13.0 |
| 90% CAPMUL MCM, 10% PEG 200 | 1.0 | IC | 14.4 |
| 90% CAPMUL MCM, 10% PEG 200 | 0.2 | IC | 8.7 |
| 95% CAPMUL MCM, 5% PPG | 1.0 | IC | 15.0 |
| 95% CAPMUL MCM, 5% PPG | 0.2 | IC | 10.0 |
| CAPMUL MCM | 1.0 | IC | 8.9 |

[a]acetic acid

Figure 2:
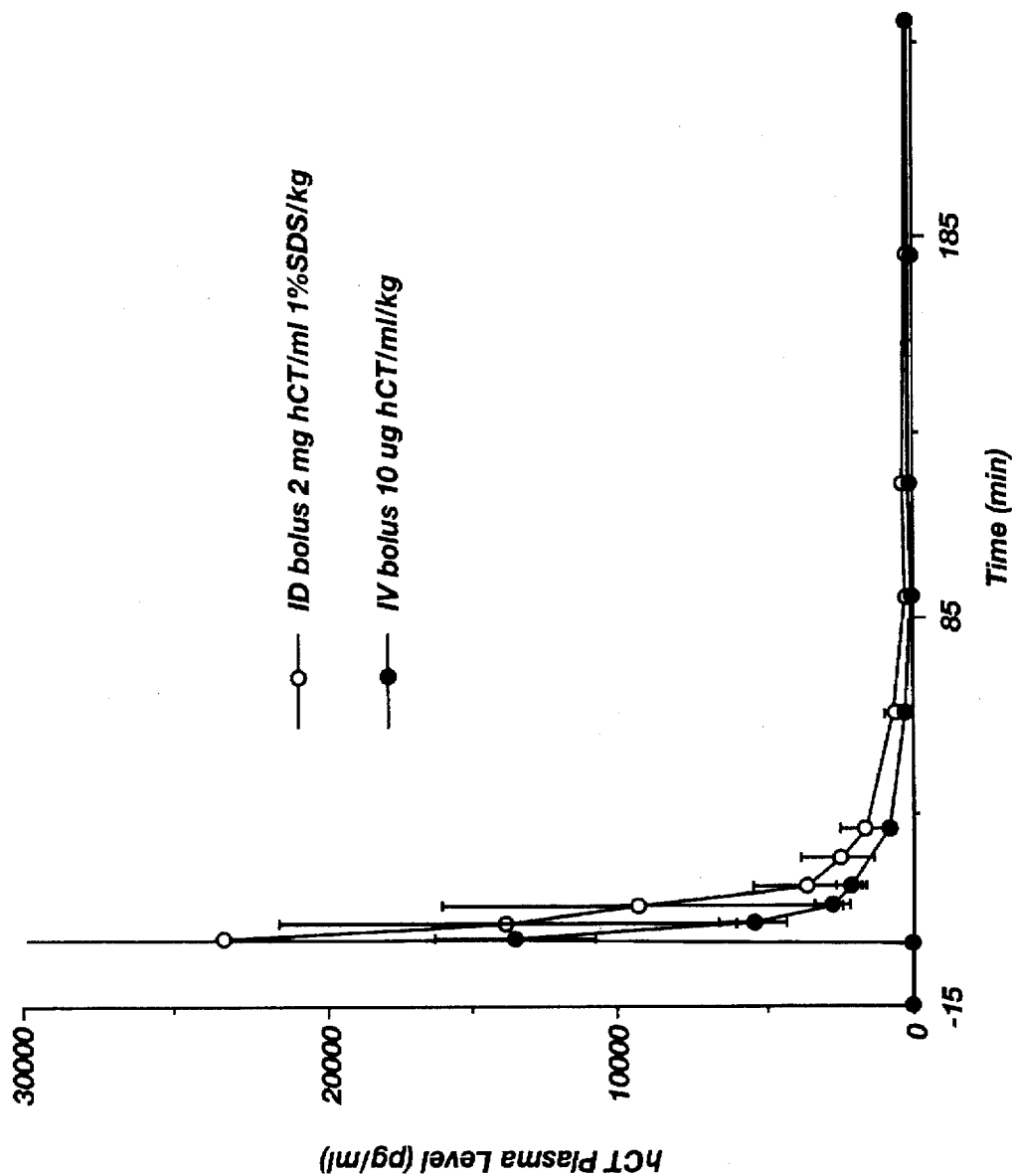
FIG. 2 shows plasma human calcitonin concentrations after bolus intravenous (IV) or bolus intraduodenal (ID) administration: ○—ID bolus of 2 mg hCT/ml 1% SDS/kg; ●—IV bolus of 10 µg hCT/ml/kg.

Administration of hCT in dilute acetic acid resulted in no detectable duodenal absorption. The stable formulation containing hCT in dilute acetic acid and 1% SDS yielded a bioavailability of about 1% by ID administration, which is relatively high for ID delivery and absorption of a peptide (FIG. 2).

Figure 3A:
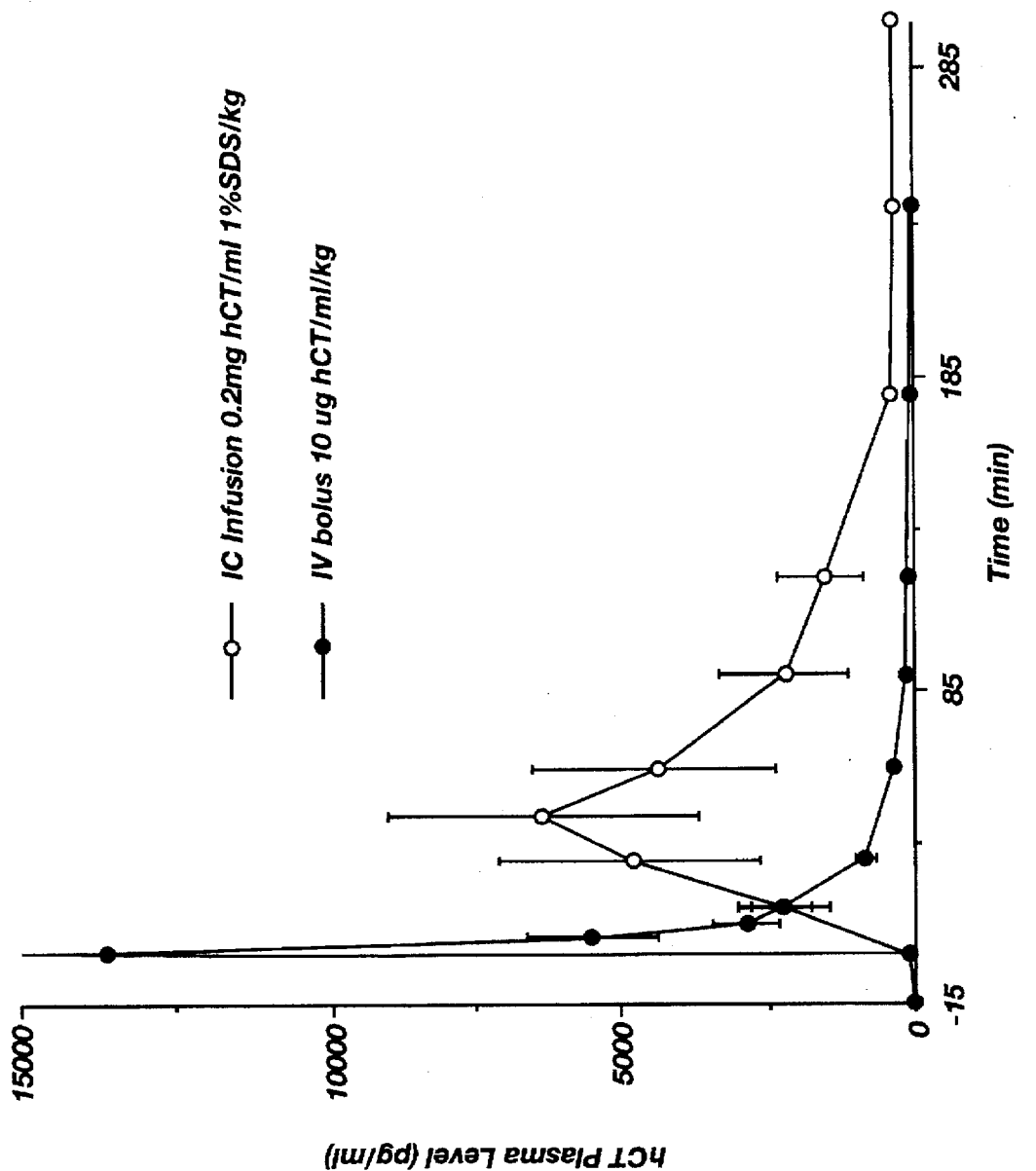
FIGS. 3A–B show plasma hCT levels (FIG. 3A) and corresponding plasma calcium levels (FIG. 3B) after bolus IV or 1 hour intracolonic (IC) infusion administration of hCT formulations: ○—IC infusion of 0.2 mg hCT/ml 1% SDS/kg; ●—IV bolus of 10 µg hCT/ml/kg.
Figure 3B:
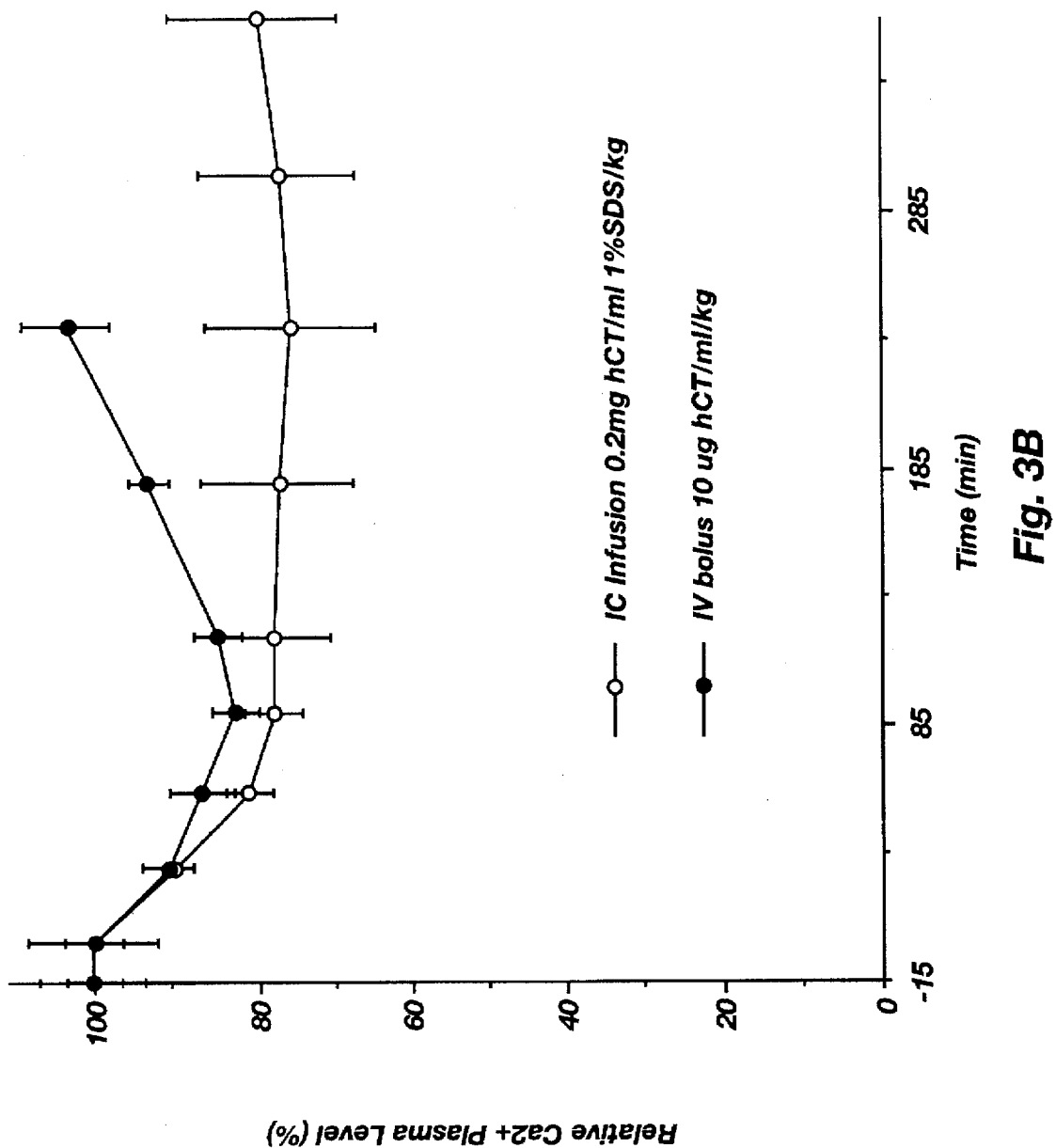
Figure 4B:
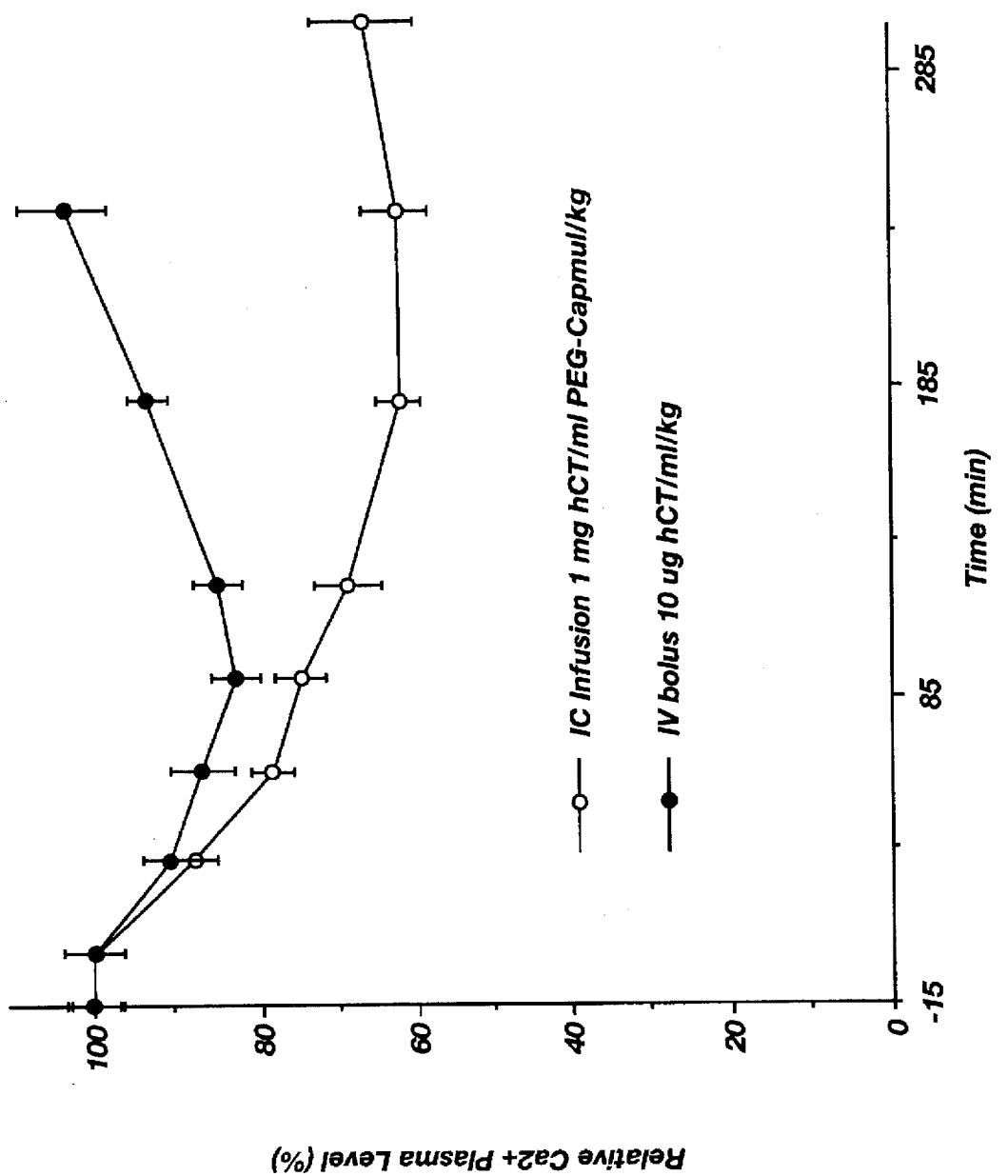
Figure 5B:
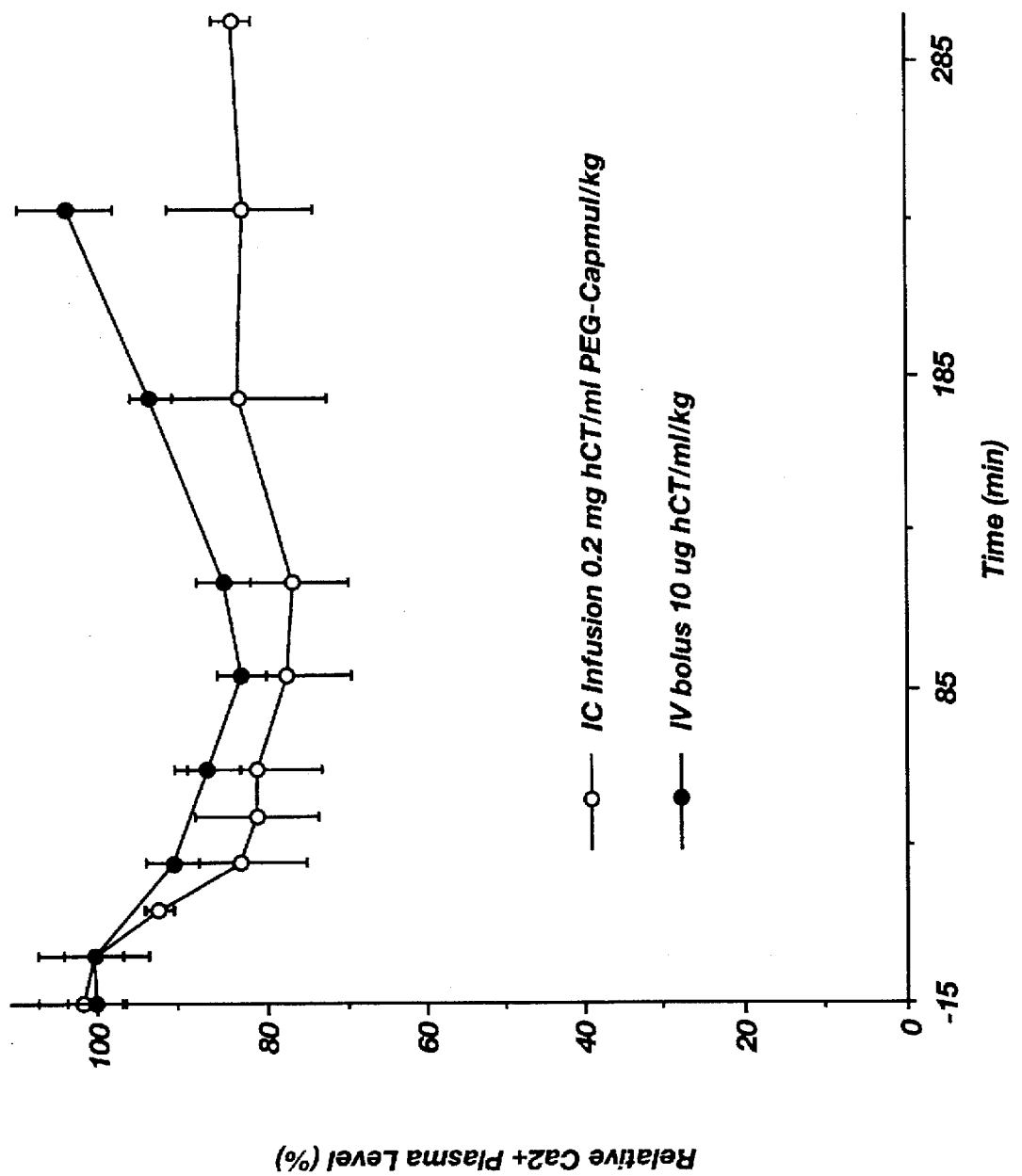

To further increase bioavailability of hCT by oral delivery, intracolonic delivery was also investigated. To better mimic calcitonin release from an oral dosage form and to avoid sudden changes in the intestinal lumen, a one hour infusion rather than bolus administration was used. As shown in Table 4, a formulation containing 1% SDS at a dose of 2 mg hCT/kg resulted in a bioavailability more than 10-fold higher than a comparable formulation administered by the ID route. When the calcitonin dose was decreased 10-fold (0.2 mg/kg), this bioavailability value was preserved (Table 4, FIG. 3A), while the blood calcium lowering, pharmacological effect of calcitonin remained significant (FIG. 3B).

Figure 6A:
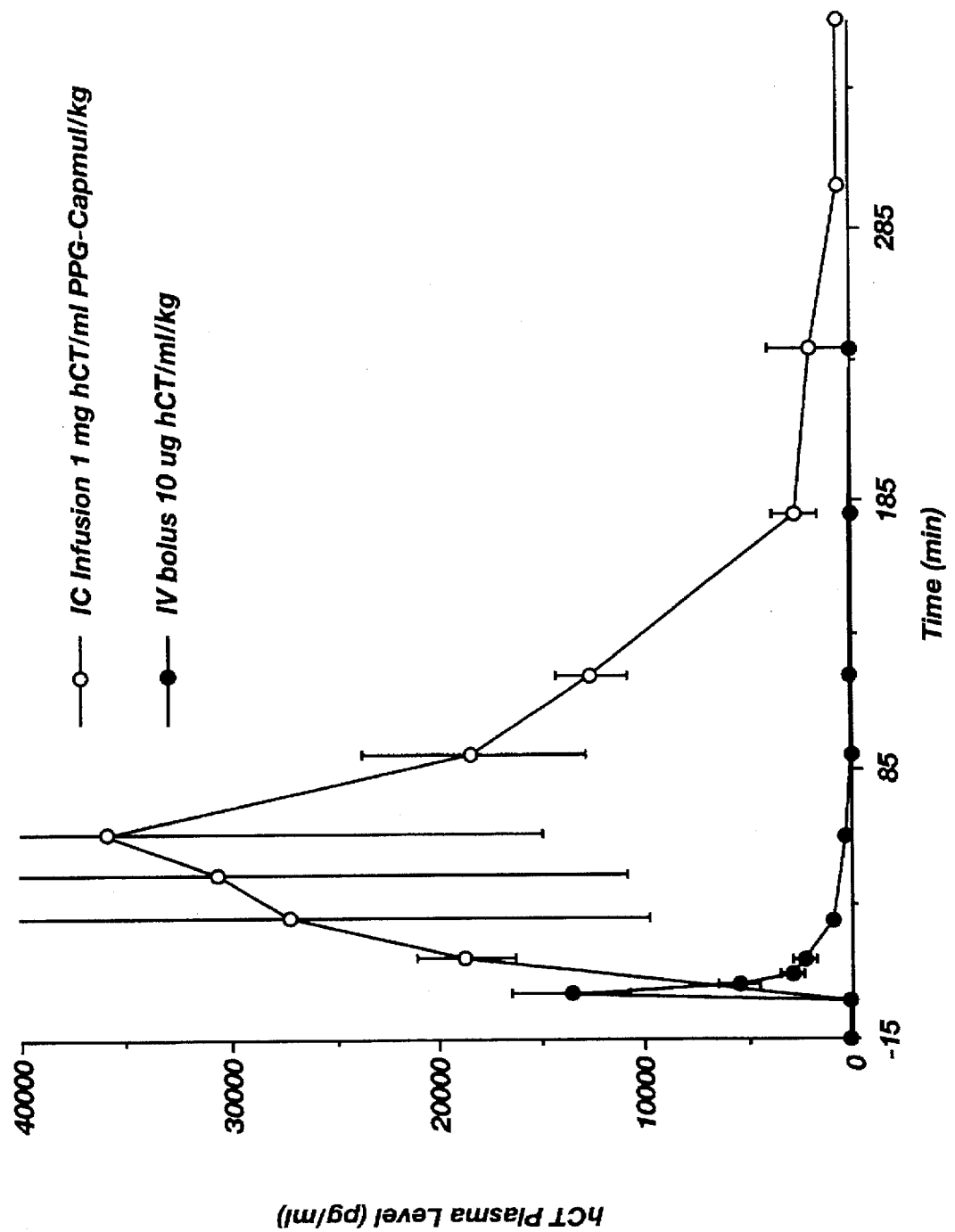
FIGS. 6A–B show plasma hCT levels (FIG. 6A) and corresponding plasma calcium levels (FIG. 6B) after bolus IV or 1 hour IC infusion administration of hCT formulations: ○—IC infusion of 1.0 mg hCT/ml 95% (v/v) CAPMUL MCM, 5% (v/v) propylene glycol/kg; ●—IV bolus of 10 µg hCT/ml/kg.
Figure 6B:
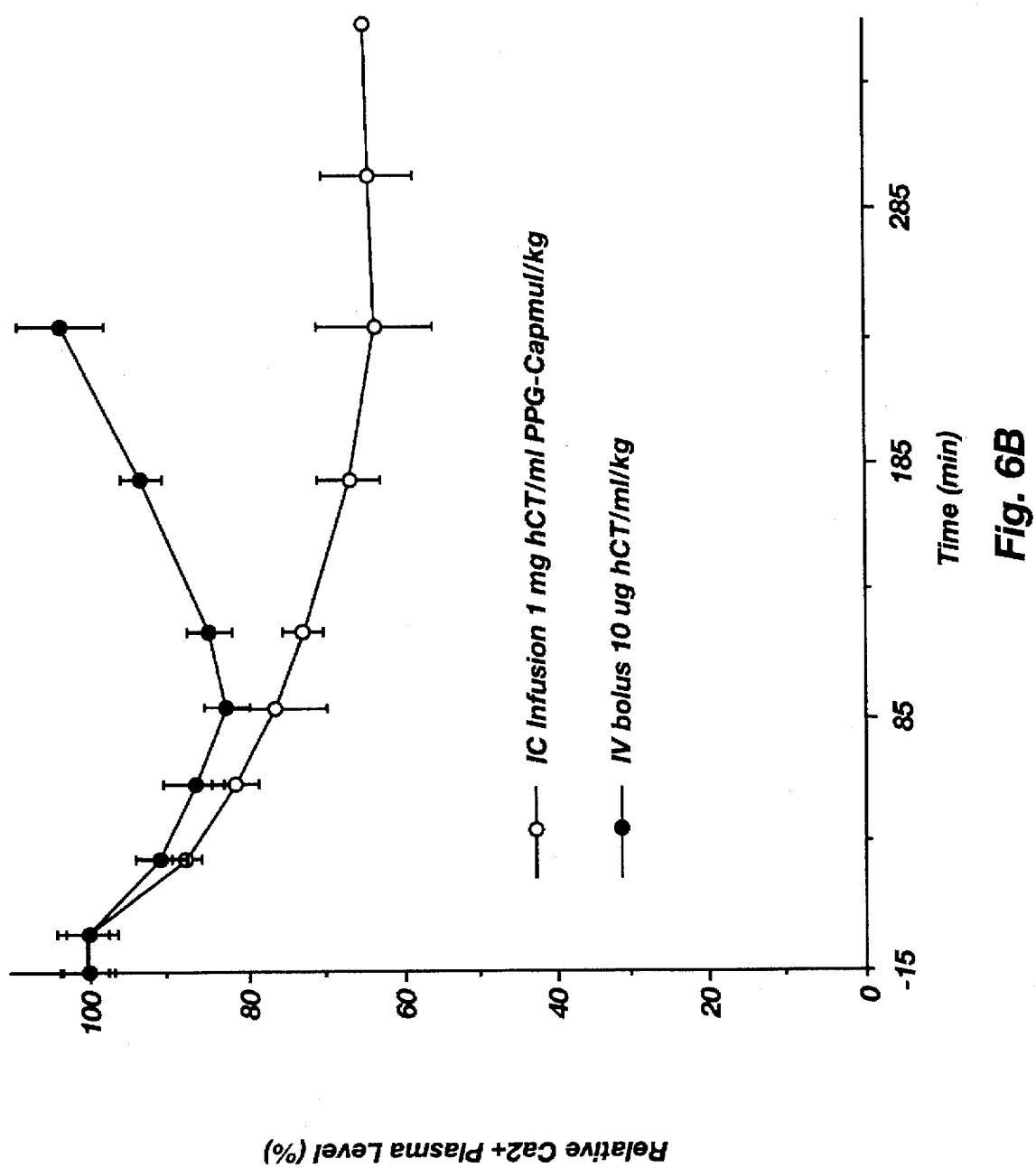

Table 4 also shows that formulations based on medium chain mono- and di-glycerides are very efficient in enhancing therapeutic calcitonin intracolonic absorption with significant pharmacological effect. Bioavailability values for CAPMUL MCM/PEG 200 formulations at two different doses showed significant IC absorption. Moreover, pharmacokinetic and pharmacodynamic IC profiles (FIGS. 4A–B and 5A–B) closely mimic profiles observed for intramuscular injections of calcitonin. Similarly, bioavailability values for CAPMUL MCM/propylene glycol (PPG) formulations at two different doses also showed significant IC absorption (FIGS. 6A–B) and thus bioavailability values (Table 4). Moreover, a formulation of hCT dissolved in CAPMUL MCM alone also provided a high bioavailability value.

For protection of hCT against the low pH and proteolytic enzymes of gastric juice in the stomach during oral adminstration, many well characterized coating materials are known in the art and are currently in use with commercially available tablets and capsules. Thus, it is feasible to deliver hCT by oral administration of both solid and liquid formulations of hCT into the small intestine using pH-sensitive coatings, such as EUDRAGIT (Rohm Tech Inc., Malden, Mass.). Many recently published reports show that the large intestine (e.g. colon) is better suited to peptide absorption. To ensure colon-specific delivery, a time-controlled release approach, e.g. a tablet or capsule coated with three different polymeric coatings, can be used and can possess prolonged release characteristics. This is possible because of relatively constant small intestine transit time of 4–5 hours for different dosage forms, as is well known in the art. Alternative approaches are currently being developed, such as azopolymer-based or dextran hydrogel-based coatings that can only disintegrate in the presence of colonic microflora.

We claim:

1. A human-calcitonin-containing liquid composition for stable storage of human calcitonin for at least about 6 months at about 4°–25° C. and for intestinal delivery of human calcitonin comprising a selected concentration of human calcitonin dissolved in a liquid medium selected from the group consisting of (a) an aqueous mixture of an effective amount of SDS and an effective amount of an organic acid; and (b) about 90–100% by volume of a mixture of $C_8/C_{10}$ mono- and di-glycerides and about 0–10% by volume of a polar, nonaqueous solvent.

2. The composition of claim 1 wherein said liquid medium is an aqueous mixture of an effective amount of SDS and an effective amount of an organic acid.

3. The composition of claim 2 wherein said organic acid is selected from the group consisting of formic acid, acetic acid, ascorbic acid, malonic acid, glutaric acid, adipic acid, citric acid, L-α-tartaric acid, DL-tartaric acid, ethylenediamine tetraacetic acid, and phenol.

4. The composition of claim 3 wherein said selected concentration of human calcitonin is up to about 10 mg/ml.

5. The composition of claim 4 wherein said effective amount of SDS is about 0.24% to 10% by weight and said effective amount of organic acid is about 0.005% to 1% by weight.

6. The composition of claim 5 wherein said selected concentration of human calcitonin is about 0.05 to 2 mg/ml.

7. The composition of claim 6 wherein said effective amount of SDS is about 0.24% to 1% by weight and said effective amount of organic acid is about 0.01% to 1% by weight.

8. The composition of claim 7 wherein said organic acid is acetic acid.

9. The composition of claim 1 wherein said liquid medium is about 90–100% by volume of a mixture of $C_8/C_{10}$ mono- and di-glycerides and about 0–10% by volume of a polar, nonaqueous solvent.

10. The composition of claim 9 wherein said liquid medium is a mixture of $C_8/C_{10}$ mono- and di-glycerides.

11. The composition of claim 9 wherein said liquid medium is about 90–99% by volume of a mixture of $C_8/C_{10}$ mono- and di-glycerides and about 1–10% by volume of a polar, nonaqueous solvent.

12. The composition of claim 11 wherein said polar, nonaqueous solvent is a member selected from the group consisting of ethylene glycol, propylene glycol, polyethylene glycol 200, dimethylformamide, and dimethylsulfoxide.

13. A method for delivering human calcitonin for intestinal absorption into the body comprising the steps of:
(a) providing a human-calcitonin-containing liquid composition comprising a selected concentration of human calcitonin dissolved in a liquid medium selected from the group consisting of (i) an aqueous mixture of an effective amount of SDS and an effective amount of an organic acid; and (ii) about 90–100% by volume of a mixture of $C_8/C_{10}$ mono- and di-glycerides and about 0–10% by volume of a polar, nonaqueous solvent; and
(b) administering said human-calcitonin-containing liquid composition such that said human-calcitonin-containing liquid contacts the intestinal mucosa and said human calcitonin is absorbed therethrough.

14. The method of claim 13 wherein said liquid medium is an aqueous mixture of an effective amount of SDS and an effective amount of an organic acid.

15. The method of claim 14 wherein said organic acid is a member selected from the group consisting of formic acid, acetic acid, ascorbic acid, malonic acid, glutaric acid, adipic acid, citric acid, L-α-tartaric acid, DL-tartaric acid, ethylenediamine tetraacetic acid, and phenol.

16. The method of claim 15 wherein said selected concentration of human calcitonin is up to about 10 mg/ml.

17. The method of claim 16 wherein said effective amount of SDS is about 0.24% to 10% by weight and said effective amount of organic acid is about 0.005% to 1% by weight.

18. The method of claim 17 wherein said selected concentration of human calcitonin is about 0.05 to 2 mg/ml.

19. The method of claim 18 wherein said effective amount of SDS is about 0.24% to 1% by weight and said effective amount of organic acid is about 0.01% to 1% by weight.

20. The method of claim 19 wherein said organic acid is acetic acid.

21. The method of claim 13 wherein said liquid medium is about 90–100% by volume of a mixture of $C_8/C_{10}$ mono- and di-glycerides and about 0–10% by volume of a polar, nonaqueous solvent.

22. The method of claim 21 wherein said liquid medium is a mixture of $C_8/C_{10}$ mono- and di-glycerides.

23. The method of claim 21 wherein said liquid medium is about 90–99% by volume of a mixture of $C_8/C_{10}$ mono- and di-glycerides and about 1–10% by volume of a polar, nonaqueous solvent.

24. The method of claim 23 wherein said polar, nonaqueous solvent is a member selected from the group consisting of ethylene glycol, propylene glycol, polyethylene glycol 200, dimethylformamide, and dimethylsulfoxide.

25. The method of claim 13 wherein administering step comprises orally administering said human-calcitonin-containing composition.

* * * * *